United States Patent [19]

Schirmer et al.

[11] Patent Number: 4,723,034
[45] Date of Patent: Feb. 2, 1988

[54] STILBENE DERIVATIVES, AND FUNGICIDES WHICH CONTAIN THESE COMPOUNDS

[75] Inventors: Ulrich Schirmer, Heidelberg; Stefan Karbach, Ludwigshafen; Ernst-Heinrich Pommer, Limburgerhof; Eberhard Ammermann, Ludwigshafen; Wolfgang Steglich, Bonn-Roettgen; Barbara A. M. Schwalge, Lohmar; Timm Anke, Kaiserlautern, all of Fed. Rep. of Germany

[73] Assignee: BASF Aktiengesellschaft, Ludwigshafen, Fed. Rep. of Germany

[21] Appl. No.: 867,571

[22] Filed: May 28, 1986

[30] Foreign Application Priority Data

May 30, 1985 [DE] Fed. Rep. of Germany ....... 3519280

[51] Int. Cl.[4] .............................................. C07C 69/76
[52] U.S. Cl. .......................................... 560/60; 560/9; 560/12; 560/14; 560/23; 560/21; 558/12; 558/414; 514/532; 514/539
[58] Field of Search ................... 560/60, 9, 12, 14, 23, 560/21; 558/12, 414; 514/532, 539

[56] References Cited

FOREIGN PATENT DOCUMENTS 0044448 1/1982 European Pat. Off. ............. 69/734
0178826 4/1986 European Pat. Off. ............. 560/60

OTHER PUBLICATIONS

Chemical Week, Jun. 21, 1972, p. 46.
Schirmer et al., U.S. Ser. No. 865,406, Chemische Berichte, vol. 111, pp. 2779-2784.

Primary Examiner—Paul J. Killos
Attorney, Agent, or Firm—Keil & Weinkauf

[57] ABSTRACT

Stilbene derivatives of the formula

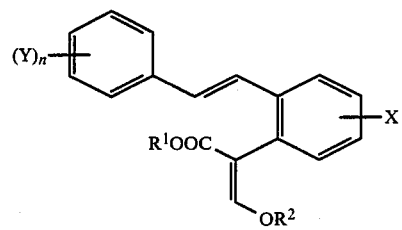

where $R^1$ and $R^2$ independently of one another are each $C_1$-$C_8$-alkyl, X is hydrogen, halogen, $C_1$-$C_4$-alkoxy, trifluoromethyl, cyano or nitro, Y is hydrogen, alkyl, haloalkyl, alkoxyalkyl, cycloalkyl, aralkyl, aryl, aryloxy, halogen, an unsubstituted or substituted $C_4H_4$ chain which is fused to the benzene radical, alkoxy, haloalkoxy, $NO_2$, alkylthio, thiocyanato, cyano, aralkyloxy, aryloxymethyl,

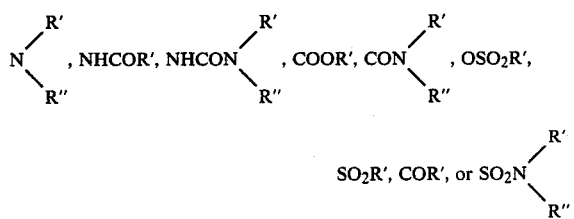

and R' and R" independently of one another are each hydrogen, alkyl, alkoxy, alkylthio or cycloalkyl or are each phenyl which is unsubstituted or substituted by alkyl, halogen or alkoxy, and n is from 1 to 4, and fungicides containing these compounds.

6 Claims, No Drawings

STILBENE DERIVATIVES, AND FUNGICIDES WHICH CONTAIN THESE COMPOUNDS

The present invention relates to novel stilbene derivatives, and fungicides which contain these compounds.

It is known that N-trichloromethylthio tetrahydrophthalimide can be used as a fungicide in agriculture, fruit growing and horticulture (Chem. Week, June 21, 1972, page 46). However, the known agent can only be used prior to infection and, at low application rates, its action does not meet practical requirements.

We have found that novel stilbene derivatives of the formula

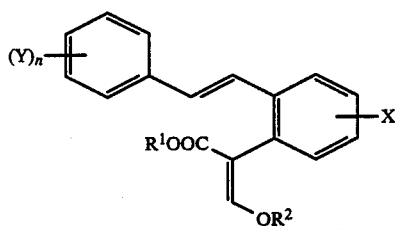

where $R^1$ and $R^2$ independently of one another are each $C_1$–$C_8$-alkyl, X is hydrogen, halogen, $C_1$–$C_4$-alkoxy, trifluoromethyl, cyano or nitro, Y is hydrogen, alkyl, haloalkyl, alkoxyalkyl, cycloalkyl, aralkyl, aryl, aryloxy, halogen, an unsubstituted or substituted $C_4H_4$ chain which is fused to the benzene radical, alkoxy, haloalkoxy, $NO_2$, alkylthio, thiocyanato, cyano, aralkyloxy, aryloxymethyl,

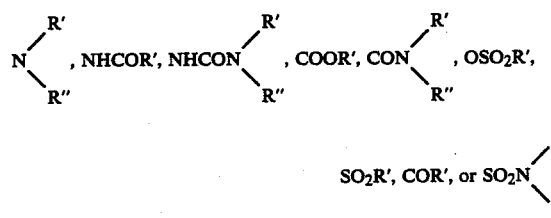

and R′ and R″ independently of one another are each hydrogen, alkyl, alkoxy, alkylthio or cycloalkyl or are each phenyl which is unsubstituted or substituted by alkyl, halogen or alkoxy, and n is from 1 to 4, have an excellent fungicidal action.

In the general formula, $R^1$ and $R^2$ may each be, for example, straight-chain or branched $C_1$–$C_8$-alkyl (eg. methyl, ethyl, isopropyl, n-propyl, n-butyl, sec-butyl, tert-butyl, isobutyl, sec-pentyl, n-hexyl, α-ethyl-n-hexyl or n-octyl), X may be, for example, hydrogen, halogen (eg. fluorine, chlorine or bromine), $C_1$–$C_4$-alkoxy (eg. methoxy or n-butoxy), trifluoromethyl, cyano or $NO_2$, Y may be, for example, hydrogen, $C_1$–$C_{12}$-alkyl (eg. methyl, ethyl, tert-butyl or dodecyl), halo-$C_1$–$C_4$-alkyl (eg. trifluoromethyl), $C_1$–$C_4$-alkoxy-$C_1$–$C_4$alkyl (eg. methoxymethyl), $C_5$–$C_8$-cycloalkyl (eg. cyclohexyl), aralkyl (eg. benzyl), aryl (eg. phenyl), aryloxy (eg. phenoxy), halogen (eg. fluorine, chlorine, bromine or iodine), an unsubstituted or substituted $C_4H_4$ chain which is fused to the benzene ring to form an unsubstituted or substituted naphthyl ring, $C_1$–$C_6$-alkoxy (eg. isopropoxy or hexyloxy), halo-$C_1$–$C_4$-alkoxy (eg, 1,1,2,2-tetrafluoroethoxy), $C_1$–$C_4$-alkylthio (eg. methylthio), thiocyanato, cyano, $NO_2$, aralkyloxy (benzyloxy, phenethyloxy), aryloxymethyl (phenoxymethyl),

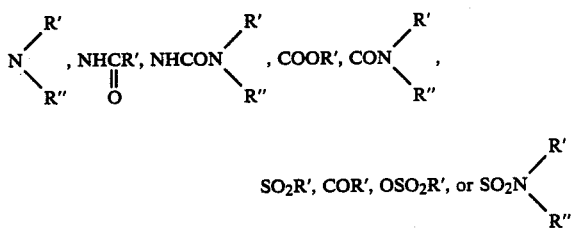

and R′ and R″ independently of one another are each hydrogen, $C_1$–$C_4$-alkyl (eg. methyl or ethyl), $C_1$–$C_4$alkoxy (eg. methoxy or tert-butoxy), $C_1$–$C_4$-alkylthio (eg. methylthio) or $C_5$–$C_8$-cycloalkyl (eg. cyclohexyl) or are each phenyl which is unsubstituted or substituted by $C_1$–$C_4$-alkyl, halogen or $C_1$–$C_4$-alkoxy (eg. phenyl, 3-chlorophenyl, 4-methylphenyl or 3-methoxyphenyl).

The novel fungicidal stilbene derivatives may be obtained as E or Z isomers at both double bonds. The stereoisomers can be separated, for example by column chromatography, or isolated in pure form on the basis of solubility differences. The pure isomers may be converted to the other isomers by conventional methods. Both the pure isomers and the mixtures thereof are embraced by the present invention. Not only the diastereoisomer mixtures, but also the pure isomers and the mixtures thereof obtained on synthesis are suitable for use as fungicides.

The novel compounds can be prepared, for example, by the following process:

A 2-methylphenylacetate of the general formula

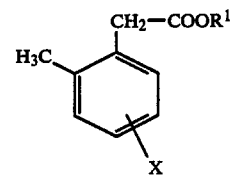

is reacted with methyl formate and sodium hydride in an inert solvent by the procedure described by Wislicenus (Liebigs Annalen 424 (1921), 215) and ibid. 413 (1917), 206). The resulting compound of the general formula

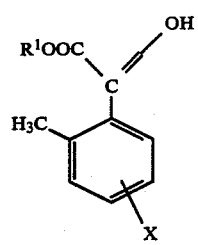

is reacted with an alkylating agent in the presence of a base in a solvent (eg. acetone) to give an α-(2-methylphenyl)-β-alkoxyacrylate

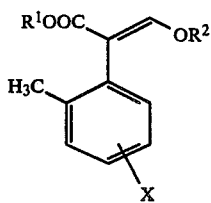

in which R¹, R² and X have the above meanings.

Bromination of this compound with N-bromosuccinimide (Horner and Winkelmann, Angew. Chemie 71 (1959), 349) gives an α-(2-bromomethylphenyl)-β-alkoxyacrylate, which reacts with a trialkyl phosphite to form a phosphonate of the general formula

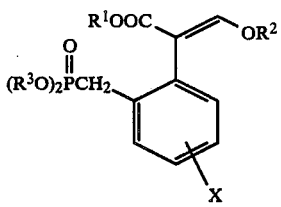

where R¹, R² and X have the above meanings and R³ is $C_1$–$C_8$-alkyl (Houben-Weyl, Methoden der organischen Chemie 12/1, 433 et seq. (1963)).

The above phosphonates are reacted with unsubstituted or substituted benzaldehydes to give the novel stilbene derivatives:

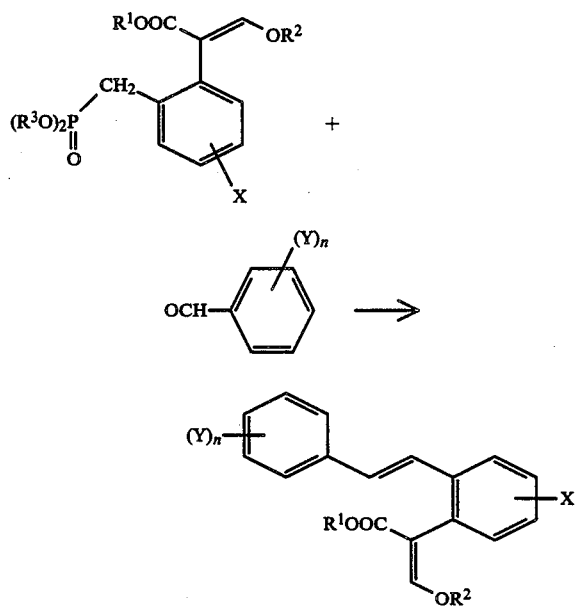

(cf. Wadsworth and Emmons, J. Amer. Chem. Soc. 83 (1961), 1732).

The Examples which follow illustrate the synthesis of the novel compounds.

METHOD A

Methyl α-(2-methylphenyl)-β-methoxyacrylate 16.5 g of methyl 2-methylphenylacetate are dissolved in 10 ml of methyl formate, and the solution is slowly added dropwise to a suspension of 3 g of sodium hydride in 150 ml of absolute ether. The mixture is refluxed for 4 hours, after which it is acidified with dilute HCl, and the organic phase is separated off, washed with water, dried over MgSO₄ and evaporated down to give 13.8 g of a pale yellow oil (methyl α-formyl-(2-methylphenyl)-acetate), which is refluxed together with 5.8 ml of dimethyl sulfate, 10.9 g of potassium carbonate and 70 ml of acetone for 1 hour. The mixture is filtered, the filtrate is evaporated down and the residue is taken up in ether, after which the solution is washed with dilute aqueous ammonia and several times with water. The ether is stripped off to give 11.3 g of crude methyl α-(2-methylphenyl)-β-methoxyacrylate of boiling point 102°–108° C./0.05.

NMR spectrum in CDCL₃: 7.53; s, 1H; 7.16–7.36; bs, 4H; 3.64; s, 3H, 3.73; s, 3H; 2.16; s, 3H.

METHOD B

Methyl α-(2-bromomethylphenyl)-β-methoxyacrylate 20.6 g of the methyl α-(2-methylphenyl)-β-methoxyacrylate obtained as described in method A, 17.65 g of N-bromosuccinimide, 0.2 g of azobisisobutyronitrile and 150 ml of CCl₄ are slowly heated to 90° C. and kept at this temperature until all of the succinimide floats on the solvent. The mixture is filtered, the filtrate is evaporated down, and the oil which remains is dissolved in about 5 ml of acetone and brought to crystallization with n-hexane. 27.5 g of colorless crystals of melting point 86°–87° C. are obtained.

METHOD C

Dimethyl 2-(α-methoxy-β-methoxycarbonylvinyl)-benzylphosphonate 28.5 g of ethyl α-(2-bromomethylphenyl)-β-methoxyacrylate are refluxed with 11.8 ml of trimethyl phosphite and 6.5 ml of toluene for one hour. The reaction mixture is carefully evaporated down under reduced pressure, and the oil which remains is dissolved in 5 ml of ether and brought to crystallization in n-hexane. 27.3 g of colorless crystals of melting point 95°–97° C. are obtained.

The following compounds can be prepared in a similar manner:

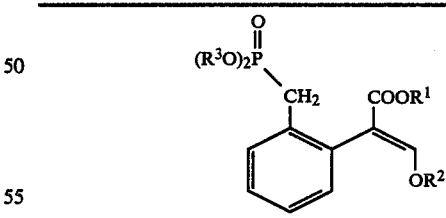

| R¹ | R² | R³ | Mp. °C./NMR |
|---|---|---|---|
| CH₃ | CH₃ | C₂H₅ | resin 53–56 |
| C₂H₅ | CH₃ | CH₃ | resin |
| i-C₃H₇ | CH₃ | CH₃ | resin |
| n-C₆H₁₃ | CH₃ | CH₃ | |
| CH₃ | C₂H₅ | CH₃ | 103–104 |
| CH₃ | i-C₃H₇ | CH₃ | |
| CH₃ | n-C₆H₁₃ | CH₃ | |
| CH₃ | s-C₄H₉ | CH₃ | |
| n-C₄H₉ | CH₃ | CH₃ | resin |
| n-C₃H₇ | CH₃ | CH₃ | |
| s-C₄H₉ | CH₃ | CH₃ | |
| CH₃ | n-C₃H₇ | CH₃ | |
| CH₃ | CH₃ | C₄H₉ | |

-continued

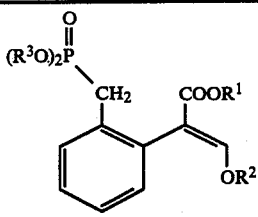

| R¹ | R² | R³ | Mp. °C./NMR |
|---|---|---|---|
| CH₃ | CH₃ | i-C₃H₇ | |
| CH₃ | CH₃ | n-C₆H₁₃ | oil |

EXAMPLE 1

2-(α-Methoxy-β-methoxycarbonylvinyl)-stilbene 3.14 g of dimethyl 2-(α-methoxy-β-methoxycarbonylvinyl)-benzylphosphonate dissolved in 7 ml of absolute tetrahydrofuran (THF) are added dropwise to 0.3 g of sodium hydride in 5 ml of absolute THF at 0° C. After from 20 to 30 minutes, 1.1 ml of benzaldehyde are added, and the mixture is allowed to warm up to 20° C. and then refluxed for 5 hours. It is cooled and then evaporated down, and 15 ml of water and 70 ml of ether are added. The organic phase is then extracted by shaking 3 times with 15 ml of 10% strength by weight aqueous NaHCO₃ solution in each case and 3 times with saturated NaCl solution and is dried over MgSO₄ and evaporated down, and the product is finally recrystallized from chloroform/hexane. 1.7 g of colorless crystals of melting point 107°–109° C. are obtained (compound No. 1).

NMR spectrum in CDCl₃: 7.67; s, 1H; 7.0–7.89; m, 11H; 3.69; s, 3H; 3.82; s, 3H.

The compounds below can be prepared in a similar manner:

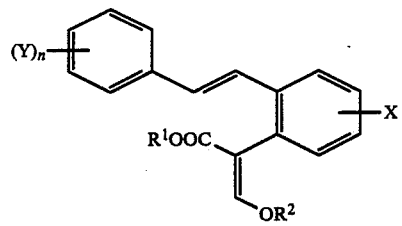

| No. | R¹ | R² | X | (Y)ₙ | M.p. °C./NMR |
|---|---|---|---|---|---|
| 1 | CH₃ | CH₃ | H | H | 107–109 |
| 2 | C₂H₅ | CH₃ | H | H | |
| 3 | i-C₃H₇ | CH₃ | H | H | |
| 4 | nC₆H₁₃ | CH₃ | H | H | |
| 5 | n-C₄H₉ | CH₃ | H | H | |
| 6 | n-C₃H₇ | CH₃ | H | H | |
| 7 | s-C₄H₉ | CH₃ | H | H | |
| 8 | CH₃ | C₂H₅ | H | H | |
| 9 | CH₃ | i-C₃H₇ | H | H | |
| 10 | CH₃ | n-C₆H₁₃ | H | H | |
| 11 | CH₃ | n-C₃H₇ | H | H | |
| 12 | CH₃ | s-C₄H₉ | H | H | |
| 13 | CH₃ | CH₃ | H | H | |
| 14 | CH₃ | CH₃ | 3-Cl | H | |
| 15 | CH₃ | CH₃ | 4-Cl | H | |
| 16 | CH₃ | CH₃ | 5-Cl | H | |
| 17 | CH₃ | CH₃ | 6-Cl | H | |
| 18 | CH₃ | CH₃ | 5-OCH₃ | H | |
| 19 | CH₃ | CH₃ | 5-CF₃ | H | |
| 20 | CH₃ | CH₃ | 5-CN | H | |
| 21 | CH₃ | CH₃ | 5-NO₂ | 4-CH₃ | |
| 22 | CH₃ | CH₃ | 6-NO₂ | H | |
| 23 | CH₃ | CH₃ | H | 4-t-C₄H₉ | |
| 24 | CH₃ | CH₃ | H | 4-C₂H₅ | |
| 25 | CH₃ | CH₃ | H | 4-CH₃ | 138–139 |
| 26 | CH₃ | CH₃ | H | 2-CH₃ | 156–158 |
| 27 | CH₃ | CH₃ | H | 3-CH₃ | 95–97 |
| 28 | CH₃ | CH₃ | H | 2-Cl | 147–148 |
| 29 | CH₃ | CH₃ | H | 3-Cl | 110–111 |
| 30 | CH₃ | CH₃ | H | 4-Cl | 113–115 |
| 31 | CH₃ | CH₃ | H | 2,4-Cl₂ | 134–136 |
| 32 | CH₃ | CH₃ | H | 3,5-Cl₂ | 144–147 |
| 33 | CH₃ | CH₃ | H | 2-F | 69–70 |
| 34 | CH₃ | CH₃ | H | 3-F | 103–105 |
| 35 | CH₃ | CH₃ | H | 4-F | 137–140 |
| 36 | CH₃ | CH₃ | H | 3-CF₃ | 75–77 |
| 37 | CH₃ | CH₃ | H | 4-CF₃ | 124–125 |
| 38 | CH₃ | CH₃ | H | 4-Br | 138–139 |
| 39 | CH₃ | CH₃ | H | 3-phenoxy | 85–87 |
| 40 | CH₃ | CH₃ | H | 4-phenoxy | |
| 41 | CH₃ | CH₃ | H | 2-OCH₃ | 60–62 |
| 42 | CH₃ | CH₃ | H | 3-OCH₃ | 102–103 |
| 43 | CH₃ | CH₃ | H | 4-OCH₃ | 125–127 |
| 44 | CH₃ | CH₃ | H | 4-O(t)-C₄H₉ | |

-continued

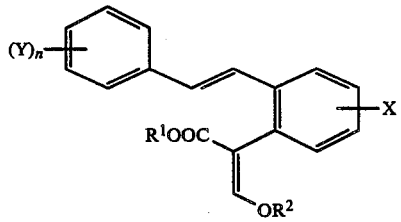

| No. | R¹ | R² | X | (Y)ₙ | M.p. °C./NMR |
|---|---|---|---|---|---|
| 45 | $CH_3$ | $CH_3$ | H | 4-O(n)-$C_4H_9$ | |
| 46 | $CH_3$ | $CH_3$ | H | 4-$CH_2OCH_3$ | |
| 47 | $CH_3$ | $CH_3$ | H | 4-I | |
| 48 | $CH_3$ | $CH_3$ | H | 2,3 (fused benzo) | resin |
| 49 | $CH_3$ | $CH_3$ | H | 3,4 (fused benzo) | 158–159 |
| 50 | $CH_3$ | $CH_3$ | H | 4-$OCHF_2$ | |
| 51 | $CH_3$ | $CH_3$ | H | 3-$OCF_2CHF_2$ | |
| 52 | $CH_3$ | $CH_3$ | H | 4-$SCH_3$ | |
| 53 | $CH_3$ | $CH_3$ | H | 4-CN | |
| 54 | $CH_3$ | $CH_3$ | H | 3-CN | |
| 55 | $CH_3$ | $CH_3$ | H | 4-SCN | |
| 56 | $CH_3$ | $CH_3$ | H | 4-$N(CH_3)_2$ | |
| 57 | $CH_3$ | $CH_3$ | H | 3-$NHCOCH_3$ | |
| 58 | $CH_3$ | $CH_3$ | H | 3-$NHCOOCH_3$ | |
| 59 | $CH_3$ | $CH_3$ | H | 4-$NHCON(CH_3)_2$ | |
| 60 | $CH_3$ | $CH_3$ | H | 4-$COOCH_3$ | |
| 61 | $CH_3$ | $CH_3$ | H | 4-$CONHCH_3$ | |
| 62 | $CH_3$ | $CH_3$ | H | 4-$SO_2CH_3$ | |
| 63 | $CH_3$ | $CH_3$ | H | 4-phenylsulfonyl | |
| 64 | $CH_3$ | $CH_3$ | H | 3-$COCH_3$ | |
| 65 | $CH_3$ | $CH_3$ | H | 4-$OSO_2CH_3$ | |
| 66 | $CH_3$ | $CH_3$ | H | 4-$SO_2N(CH_3)_2$ | |
| 67 | $CH_3$ | $CH_3$ | H | 4-NHCONH-(3-Cl-phenyl) | |
| 68 | $CH_3$ | $CH_3$ | H | 4-benzoyl | |
| 69 | $CH_3$ | $CH_3$ | H | 3-$NO_2$ | |
| 70 | $CH_3$ | $CH_3$ | H | 4-$NO_2$ | |
| 71 | $CH_3$ | $CH_3$ | H | 2-Cl-6F | |
| 72 | $CH_3$ | $CH_3$ | H | 2,4,5($CH_3$)$_3$ | |
| 73 | $CH_3$ | $CH_3$ | H | 3,4,5($OCH_3$)$_3$ | 118–121 |
| 74 | $CH_3$ | $CH_3$ | H | 2,4($CH_3$)$_2$ | |
| 75 | $CH_3$ | $CH_3$ | H | 4-i-$C_3H_7$ | |
| 76 | $CH_3$ | $CH_3$ | H | 4-phenyl | |
| 77 | $CH_3$ | $CH_3$ | H | 2,3,4-$Cl_3$ | |
| 78 | $CH_3$ | $CH_3$ | H | 2,6-$Cl_2$ | 127–128 |
| 79 | $CH_3$ | $CH_3$ | H | 3,4-$Cl_2$ | 96–98 |
| 80 | $CH_3$ | $CH_3$ | H | 3-$NO_2$4$CH_3$ | |
| 81 | $CH_3$ | $CH_3$ | H | 4-$N(C_2H_5)_2$ | |
| 82 | $CH_3$ | $CH_3$ | H | 2,4,5($OCH_3$)$_3$ | |
| 83 | $CH_3$ | $CH_3$ | H | 3,5-($OCH_3$)$_2$ | |
| 84 | $CH_3$ | $CH_3$ | H | 3-benzyloxy | 77–70 |
| 85 | $CH_3$ | $CH_3$ | H | 2,4,6($OCH_3$)$_3$ | |
| 86 | $CH_3$ | $CH_3$ | H | 4-O(n)$C_6H_{13}$ | |
| 87 | $CH_3$ | $CH_3$ | H | 2-Cl5$NO_2$ | |
| 88 | $CH_3$ | $CH_3$ | H | 3$NO_2$4Cl | 168–169 |
| 89 | $CH_3$ | $CH_3$ | H | 2-Cl6$NO_2$ | |
| 90 | $CH_3$ | $CH_3$ | H | 2-$OCF_2CHF_2$ | |
| 91 | $CH_3$ | $CH_3$ | H | 3-Br4$OCH_3$ | |
| 92 | $C_2H_5$ | $CH_3$ | H | 3-Cl | |
| 93 | $C_2H_5$ | $CH_3$ | H | 4-Cl | |
| 94 | $C_2H_5$ | $CH_3$ | H | 3,5$Cl_2$ | |

-continued

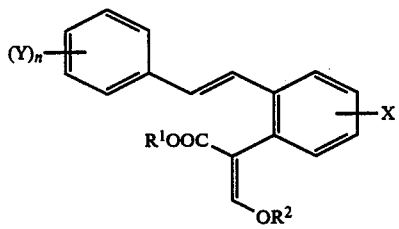

| No. | R¹ | R² | X | (Y)ₙ | M.p. °C./NMR |
|---|---|---|---|---|---|
| 95 | C₂H₅ | CH₃ | H | 4-F | |
| 96 | C₂H₅ | CH₃ | H | 4-Br | |
| 97 | C₂H₅ | CH₃ | H | 4-CH₃ | |
| 98 | C₂H₅ | CH₃ | H | 3,4-(CH₃)₂ | |
| 99 | C₂H₅ | CH₃ | H | 4-OCH₃ | |
| 100 | C₂H₅ | CH₃ | H | 3,4,5-(OCH₃)₃ | |
| 101 | C₂H₅ | CH₃ | H | 3-CH₃ | |
| 102 | C₂H₅ | CH₃ | H | 4-(t)C₄H₉ | |
| 103 | C₂H₅ | CH₃ | H | 2CH₃ | |
| 104 | CH₃ | C₂H₅ | H | 4-Cl | |
| 105 | CH₃ | C₂H₅ | H | 4-F | |
| 106 | CH₃ | C₂H₅ | H | 4-CH₃ | |
| 107 | CH₃ | C₂H₅ | H | 4-OCH₃ | |
| 108 | CH₃ | C₂H₅ | H | 4-NO₂ | |
| 109 | CH₃ | CH₃ | H | 4-benzyloxy | |
| 110 | CH₃ | CH₃ | H | 3-phenethyl | |
| 111 | CH₃ | CH₃ | H | 4-phenethyl | |
| 112 | CH₃ | CH₃ | H | 3-phenethyloxy | |
| 113 | CH₃ | CH₃ | H | 4-phenethyloxy | |
| 114 | CH₃ | CH₃ | H | 3-phenoxymethyl | |
| 115 | CH₃ | CH₃ | H | 4-phenoxymethyl | |

In general terms, the novel compounds are very effective against a broad spectrum of phytopathogenic fungi, in particular those from the class consisting of the Ascomycetes, Phycomycetes and Basidiomycetes. Some of them have a systemic action and can be used as foliar and soil fungicides.

The fungicidal compounds are of particular interest for controlling a large number of fungi in various crops or their seeds, in particular wheat, rye, barley, oats, rice, corn, cotton, soybean, coffee, sugar cane, fruit and ornamentals in horticulture, in viticulture, and in vegetables, such as cucumbers, beans and Cucurbitaceae.

The novel compounds are particularly useful for controlling the following plant diseases: *Erysiphe graminis* in cereals, *Erysiphe cichoracearum* and *Sphaerotheca fuliginea* in Cucurbitaceae, *Podosphaera leucotricha* in apples, *Uncinul necator* in vines, *Puccinia* species in cereals, *Rhizoctonia solani* in cotton, *Ustilago* species in cereals and sugar cane, *Venturia inaequalis* (scab) in apples, *Septoria nodorum* in wheat, *Pyrenophora teres* in barley, *Botrytis cinerea* (gray mold) in strawberries and vines, *Cercospora arachidicola* in groundnuts, *Pseudocercosporella herpotrichloides* in wheat and barley, *Pyricularia oryzae* in rice, *Phytophthora infectans* in potatoes and tomatoes, *Alternaria solani* in potatoes and tomatoes, *Plasmopara viticola* in vines, and *Fusarium* and *Verticillium* species in various plants.

The compounds are applied by spraying or dusting plants with the active ingredients, or treating the seeds of the plants with the active ingredients. They are applied before or after infection of the plants or seeds by the fungi.

The novel substances can be converted to the conventional formulations, such as solutions, emulsions, suspensions, dusts, powders, pastes and granules. The application form depend entirely on the purposes for which they are intended; they should at all events ensure a fine and uniform distribution of the active substance. The formulations are produced in a known manner, for example by extending the active ingredient with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (eg. xylene or benzene), chlorinated aromatics (eg. chlorobenzenes), paraffins (eg. oil fractions), alcohols (eg. methanol or butanol), ketones (eg. cyclohexanone), amines (eg. ethanolamine or dimethylformamide) and water; carriers, such as ground natural minerals (kaolins, aluminas, talc or chalk) and ground synthetic minerals (eg. highly disperse silica or silicates) emulsifiers, such as nonionic and anionic emulsifiers (eg. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient.

The application rates are from 0.05 to 3 kg or more of active ingredient per ha, depending on the type of effect desired. The novel compounds may also be employed in material protection, inter alia for controlling wood-destroying fungi, such as Coniophora puteana and Polystictus versicolor. The novel active ingredients can also be used as fungicidal components of oily wood preservatives for protecting wood against wood-discoloring fungi. They are used by treating, for example impregnating or painting, the wood with these agents.

The agents and the ready-to-use formulations prepared from them, such as solutions, emulsions, suspensions, powders, dusts, pastes or granules, are applied in a conventional manner, for example by spraying, atomizing, dusting, scattering, dressing or watering.

Examples of such formulations are:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur
dithiocarbamates and derivatives thereof, such as
ferric dimethyldithiocarbamate
zinc dimethyldithiocarbamate
zinc ethylenebisthiocarbamate
manganese ethylenebisdithiocarbamate
manganese zinc ethylenediaminebisdithiocarbamate
tetramethylthiuram disulfide
ammonia complex of zinc N,N'-ethylenebisdithiocarbamate
ammonia complex of zinc N,N-propylenebisdithiocarbamate
zinc N,N'-propylenebisdithiocarbamate and
N,N-polypropylenebis(hiocarbamyl) disulfide
nitro derivatives, such as
dinitro (1-methylheptyl)-phenyl crotonate
2-sec-butyl-4,6-dinitrophenyl-3,3-dimethylacrylate
2-sec-butyl-4,6-dinitrophenyl isopropylcarbonate and diisopropyl 5-nitroisophthalate
heterocyclic substances, such as
2-heptadecylimidazol-2-yl acetate
2,4-dichloro-6-(o-chloroanilino)-s-triazine
O,O-diethyl phthalimidophosphonothionate
5-amino-1-[bis-(dimethylamino)-phosphinyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylthiophthalimide
N-dichlorofluoromethylthio-N',N'-dimethyl-N-phenylsulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
2-thiopyridine 1-oxide
8-hydroxyquinoline and its copper salt
2,3-dihydro-5-carboxanilido-6-methyl-1,4-oxathin
2,3-dihydro-5-carboxanilido-6-methyl-1,4-oxathiin 4,4-dioxide
2-methyl-5,6-dihydro-4-H-pyran-3carboxanilide
2-methyl-furan-3-carboxanilide
2,5-dimethyl-furan-3-carboxanilide
2,4,5-trimethyl-furan-3-carboxanilide
2,5-dimethyl-N-cyclohexylfuran-3-carboxamide
N-cyclohexyl-N-methoxy-2,5-dimethyl-furan-3-carboxamide
2-methylbenzanilide
2-iodobenzanilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane 2,6-dimethyl-N-tridecyl-morpholine and its salts 2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine 1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-ylethyl]-1-H-1,2,4-triazole
N-(n-propyl)-N-(2,4,6-trichlorophenoxyethyl)-N'-imidazolylurea
1-(4-chlorophenoxy)-3,3-dimethyl-1-(1H-1,2,4-triazol-1-yl)butan-2-one
1-(4-chlorophenoxy)-3,3-dimethyl-1-(1H-1,2,4-triazol-1-yl)butan-2-ol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-fur-2-yl alanate
methyl D,L-N-(2,6-dimethylphenyl)-N-(2'-methoxyacetyl)alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropylcarbamoylhydantoin
N-(3,5-dichlorophenyl)-1,2-dimethyl-cyclopropane-1,2-dicarboximide
2-cyano-[N(ethylaminocarbonyl)-2-methoximino]-acetamide
1-[2-(2,4-dichlorophenyl)-pentyl]-1H-1,2,4-triazole and 2,4-difluoro-alpha-(1H-1,2,4-triazol-1-ylmethyl)-benzhydryl alcohol
N-(3-chlorophenyl)-5-trifluoromethylpyridine
N-(2,6-dinitrophenyl)-3-chloropyridine
N-(4-trifluoromethylphenyl)-2-aminopyridine
1-(bis-(4-fluorophenyl)-methylsilyl)-methyl-1H-1,2,4-triazole.

For the experiments below, the prior art active ingredient N-trichloromethylthiotetrahydrophthalimide (A) was used for comparison purposes.

USE EXAMPLE 1

Action on *Phytophthora infestans* in tomatoes

Leaves of potted tomatoes of the "Grosse Fleischtomate" variety were sprayed with aqueous liquors containing (dry basis) 80% of active ingredient and 20% of emulsifier. After the sprayed-on layer had dried, the leaves were infected with a zoospore suspension of *Phytophthora infestans*. The plants were then placed for 5 days in a steam-saturated chamber kept at 16° to 18° C. After this period, the disease had spread on the untreated control plants to such an extent that the fungicidal action of the compounds was able to be assessed.

The results of this experiment show that active ingredients nos. 1, 25, 26, 27, 28, 29, 34, 35, 37, 38, 39, 41, 48, 49, 73, 79 and 84, applied as 0.025 wt% spray liquors, have a better fungicidal action (95%) then prior art active ingredient A (80%).

USE EXAMPLE 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that active ingredients nos. 1, 26, 27, 29, 32, 33, 34, 35, 37, 38, 39, 42, 49, 79, 84 and 88, applied as 0.05, 0.0125 and 0.006% spray liquors, have a good fungicidal action (100%).

USE EXAMPLE 3

Action of *Pyricularia oryzae* (protective)

Leaves of pot-grown rice seedlings on the "Bahia" variety were sprayed to runoff with aqueous emulsions consisting (dry basis) of 80% of active ingredient and 20% of emulsifier, and inoculated 24 hours later with an aqueous spore suspension of Pyricularia oryzae. The plants were then set up in climatic cabinets at 22° to 24° C. and a relative humidity of 95 to 99%. The extent of fungus spread was determined after 6 days.

The results of this experiment show that active ingredient no. 1, applied as a 0.05% spray liquor, has a good fungicidal action (100%).

USE EXAMPLE 4

Action on apple scab

Young leaves of pot-grown apple seedlings of the "Golden Delicious" variety were sprayed to runoff with aqueous spray liquors containing (dry basis) 80% of active ingredient and 20% of emulsifier. After the sprayed-on layer had dried, the plants were sprayed with a spore suspension of apple scab (*Venturia inaequalis*). The inoculated plants were then set up in a climatic cabinet for 18 days at 20° to 22° C. and a relative humidity of 95%. The extent of fungus spread on the leaves was then determined.

The results show that active ingredient no. 1, when applied as a 0.0075 and 0.00375% spray liquor, had a good fungicidal action (100%).

USE EXAMPLE 5

Action on *Pyrenophora teres*

Leaves of pot-grown barley seedlings of the Asse variety were sprayed, at the two-leaf stage, to runoff with aqueous spray liquors containing (dry basis) of 80% of active ingredient and 20% of emulsifier. After 24 hours, the dried plants wer inoculated with an aqueous spore suspension of *Pyrenophora teres*, and placed for 48 hours in a climatic cabinet having a high humidity and kept at 18° C. The plants were subsequently cultivated for a further 5 days in the greenhouse at 20° to 22° C. and a relative humidity of 70%. The extent of fungus spread was then determined.

The results show that active ingredients nos. 1, 25, 26, 27, 28, 29, 33, 34, 35, 36, 39, 41, 49, 73, 78, 79, 84 and 88, applied as 0.05% spray liquors, have a good fungicidal action (97%).

USE EXAMPLE 6

Action on powdery mildew of wheat

Leaves of pot-grown wheat seedlings of the Frühgold variety were sprayed with aqueous spray liquors containing (dry basis) 80% of active ingredients and 20% of emulsifier, and, 24 hours after the spray coating had dried on, the leaves were dusted with oidia (spores) of powdery mildew of wheat (*Erysiphe graminis* var. tritici). The test plants were then placed in a greenhouse at from 20° to 22° C. and from 75 to 80% relative humidity. After 7 days, the extent of powdery mildew development was determined.

The results show that active ingredients nos. 1, 25, 26, 27, 28, 29, 32, 33, 34, 35, 36 and 37, applied as 0.025 and 0.006% spray liquors, have a good fungicidal action (97%).

We claim:

1. A stilbene derivative of the formula

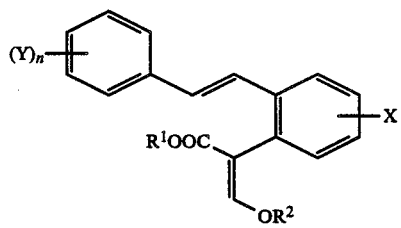

where $R^1$ and $R^2$ independently of one another are each $C_1$–$C_8$-alkyl, X is hydrogen, halogen, $C_1$–$C_4$-alkoxy, trifluoromethyl, cyano or nitro, Y is hydrogen, alkyl, haloalkyl, alkoxyalkyl, cycloalkyl, aralkyl, aryl, aryloxy, halogen, an unsubstituted $C_4H_4$ chain which is fused to the benzene radical, alkoxy, haloalkoxy, $NO_2$, alkylthio, thiocyanato, cyano, aralkyloxy, aryloxymethyl,

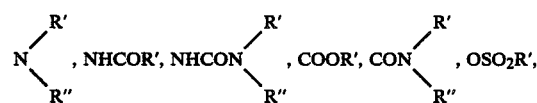

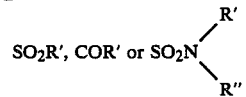

and R' and R" independently of one another are each hydrogen, alkyl, alkoxy, alkylthio or cycloalkyl or are each phenyl which is unsubstituted or substituted by alkyl, halogen or alkoxy, and n is from 1 to 4.

2. 2-(β-methoxy-alpha-methoxycarbonylvinyl)-stilbene.

3. A fungicide containing a solid or liquid carrier and an effective amount of a stilbene derivative of the formula

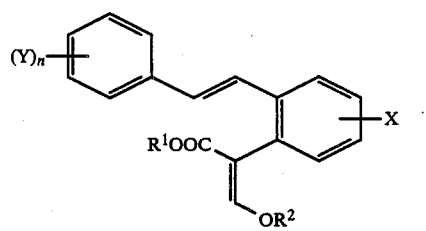

where $R^1$ and $R^2$ independently of one another are each $C_1$–$C_8$-alkyl, X is hydrogen, halogen, $C_1$–$C_4$-alkoxy, trifluoromethyl, cyano or nitro, Y is hydrogen, alkyl, haloalkyl, alkoxyalkyl, cycloalkyl, aralkyl, aryl, aryloxy, halogen, an unsubstituted $C_4H_4$ chain which is fused to the benzene radical, alkoxy, haloalkoxy, $NO_2$, alkylthio, thiocyanato, cyano, aralkyloxy, aryloxymethyl,

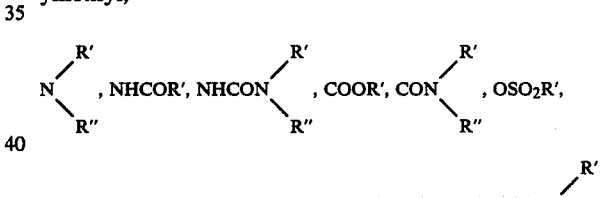

and R' and R" independently of one another are each hydrogen, alkyl, alkoxy, alkylthio or cycloalkyl or are each phenyl which is unsubstituted or substituted by alkyl, halogen or alkoxy, and n is from 1 to 4.

4. A fungicide containing a solid or liquid carrier and an effective amount of 2-(β-methoxy-alpha-methoxycarbonylvinyl)-stilbene.

5. A process for combatting fungi, wherein the fungi or the materials, plants, seed or soil threatened by fungus attack are treated with a fungicidally effective amount of a compound as set forth in claim 1.

6. The process of claim 5, wherein the compound is 2-(β-methoxy-alpha-methoxycarbonylvinyl)stillbene.

* * * * *

Adverse Decisions In Interference

Patent No. 4,723,034, Ulrich Schirmer, Stefan Karbach, Ernst-Heinrich Pommer, Eberhard Ammermann, Wolfgang Steglich, Barbara A. M. Schwalge, Timm Anke, STILBENE DERIVATIVES, AND FUNGICIDES WHICH CONTAIN THESE COMPOUNDS, Interference No. 102,733, final judgment adverse to the patentees rendered April 16, 1998 as to claims 1-6.

*(Official Gazette July 7, 1998)*